United States Patent [19]

Szentmiklósi et al.

[11] 4,035,366

[45] July 12, 1977

[54] 1-BENZAL-1,2,3,4-TETRAHYDRO-ISOQUINOLINIUM-THEOPHYLLINE-7-ACETATES

[75] Inventors: Péter Szentmiklósi; Zoltán Mészáros; László Tardos; István Hermecz; Ilona Erdélyi; Agoston Dávid; Lelle Vasvári nee Debreczy; Ágnes Horvath, all of Budapest, Hungary

[73] Assignee: Chinoin Gyogyszer-es Vegyeszeti Termekek Gyara RT, Budapest, Hungary

[21] Appl. No.: 435,591

[22] Filed: Jan. 22, 1974

[30] Foreign Application Priority Data

Jan. 25, 1973 Hungary .............................. CI 1333

[51] Int. Cl.$^2$ ..................................... C07D 473/08
[52] U.S. Cl. ................................. 260/253; 424/253
[58] Field of Search ..................................... 260/253

[56] References Cited

FOREIGN PATENT DOCUMENTS

| 1,369,374 | 7/1964 | France | 260/253 |
| 2,975M | 11/1964 | France | 260/253 |
| 3,625M | 10/1965 | France | 260/253 |

Primary Examiner—Paul M. Coughlan, Jr.
Attorney, Agent, or Firm—Karl F. Ross; Herbert Dubno

[57] ABSTRACT

1-Benzal-1,2,3,4-tetrahydro-isoquinolinium-theophylline-7-acetates are used in the manufacture of geriatric compositions.

3 Claims, No Drawings

1-BENZAL-1,2,3,4-TETRAHYDRO-ISOQUINOLINIUM-THEOPHYLLINE-7-ACETATES

This invention is directed to geriatric compositions, containing salts of dihydro- and tetrahydroisoquinoline-theophylline-7-acetic acid.

A general geriatric composition has to meet the following requirements:

it must stimulate the function of the central nervous system, improve blood circulation, improve the perfusion of the coronary vessels and stimulate the action of the heart and, improve respiration, which generally deteriorates with old age.

It should decrease the predisposition toward embolism, it should have a mild diuretic effect, and it should be absorbed well by the body when administered per os, and not cause any undesirable side effects, even when taken regularly for a long time.

It is known that several isoquinoline-derivatives spasmolytic effects of Papaverine, a classical compound for the treatment of geriatric conditions. Many pharmaceutical companies have put on the market Papaverine dragees with an active ingredient content of 100–150 mg. for geriatric purposes in recent years.

Theophylline and derivatives thereof also must be considered as for the classical treatment of geriatric conditions. This group of compounds exhibits spasmolytic, hypotensive and diuretic effects. The ethylenediamine salt of theophylline is widely used in geriatric therapy.

According to the literature (Sperimentale: Sez. Chim. Biol. 5, 6–6 (1964), French Patent Specification No. 1 369 374 and French Pat. Specification No. M 2975), there have already been attempts to make use in geriatric therapy of the therapeutical properties of the abovementioned group of compounds. These authors prepared and examined the salt of papaverine formed with theophilline-7-acetic acid. According to the results of the above tests the salt did not show any additional or potentiated effect as had been expected, but on the contrary the therapeutic effect of the papaverine decreased.

In our experiments some salts of dihydro- and tetrahydro-isoquinoline-theophylline-7-acetic acid were prepared and we have surprisingly found that the effect in some parameters was enhanced unexpectedly without any decrease of other examined parameters. Thus we have discovered a group of compounds which meets the theoretical requirements of a geriatric compositon as mentioned above.

The compounds are those of the formula (I)

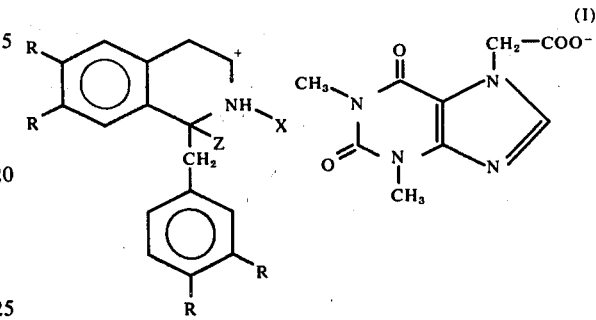

R represents a hydrogen or an alkoxy group having 1–10 carbon atoms and,

Z and X represent hydrogen or form together a valence bond.

The definition of R, Z and X remains the same throughout the specification. Where Z and X form a valency bond, the compound may appear in the two forms Ia and Ib below:

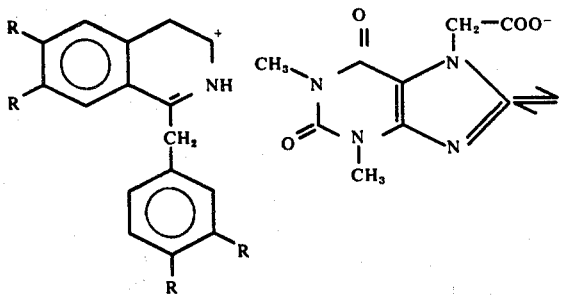

Ia

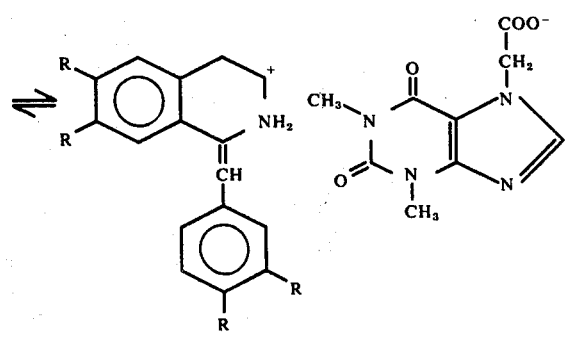

Ib

The compounds of the formula (I) are prepared by reacting a compound of the formula (II)

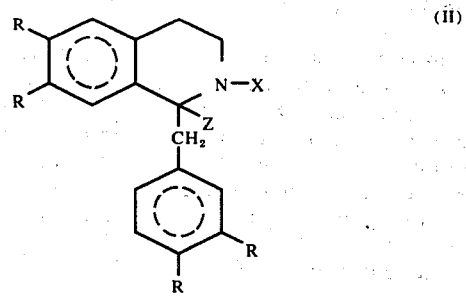

in the presence of a solvent with theophylline-7-acetic acid of the formula (III)

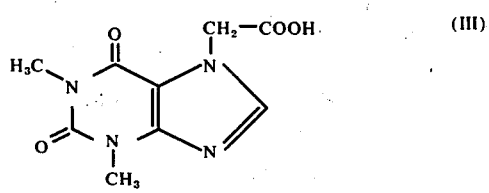

The compound of the formula (I) precipitated from the solvent after cooling is separated by filtration. As the solvent we preferably use alcohols, e.g. methanol, ethanol, n-propanol and i-propanol.

The starting materials of the formulae (II) and (III) are prepared by methods known per se.

As starting materials compounds of the formula (II) are used, wherein R stands for an alkoxy group having 1–10 carbon atoms, particularly normal-alkoxy groups containing 1–4 carbon atoms, e.g. methoxy, ethoxy, propoxy and butoxy and X and Z form together a valence bond.

As far as the toxicological and pharmacological properties of the examined compounds are concerned, the tetra-ethoxy-benzene-tetra-hydro-isoquinoline-derivative yielded best results in the animal-tests.

According to toxicological investigations the compound is absorbed well by the body, the toxicity of the compound is very low and is not higher than the toxicity of the components of the salt themselves.

The compound exhibits spasmolytic effect, hypotensive effect and inhibits convulsions, caused by electroshock. It must be emphasized that on cats the compound induces a better hypotensive effect than the dose-equivalent isoquinoline-component, while theophylline-7-acetic acid does not show any hypotensive effect at a corresponding dosage. A potentiation of the same kind can be observed in the effect on the respiratory-volume; while the theophylline-7-acetic acid does not show any effect for the indicated dosage, the isoquinoline-component decreases the respiration volume in a dosage of 1 mg./kg body weight; in a dosage of 2 of mg./kg body weight a considerable decrease of effect can be seen, and in the same dosage the compound of the present invention does not significantly influence the respiration volume.

A unit dose of the compound contains 100–300 mg. of active ingredient and the compound can be used as usual in the form of tablets, capsules or dragees or in solution, suspension or emulsion.

The compound can be used in geriatric therapy in the form of time-delay dragees, containing 100–300 mg. of active ingredient (skelton tablets, microcapsulated tablets, adsorptional tablets, multilayered tablets etc.).

The compound of the present invention can be administered for acute conditions in sterile solutions, containing 150–300 mg. of active ingredient, by injection of infusion.

Cocoa butter, contaning 100–300 mg. of the active ingredient, may also be ued to form suppositories, having a plastic base and as prepared by conventional means.

The compound of the present invention may preferably be combined with other active ingredients with other types of activity; antidepressants, tranquillizers, antihypertensive agents, diuretics, antiasthmatics, cardiac agents, and, vitamins.

Further details of the present invention may be found in the Examples.

EXAMPLE 1

2.21 g. (0.01 mole) of 1-benzal-1,2,3,4-tetrahydroisoquinoline and 2.38 g. (0.01 mole) of theophylline-7-acetic acid are dissolved under boiling in 25 ml. of n-propanol. The undissolved substances is filtered from the hot solution. The clear filtrate is crystallized while the mixture is cooled. The precipitated crystals are filtered out, covered with n-propanol and dried at room temperature. Thus 2.2 g. of 1-benzal-1,2,3,4-tetrahydroisoquinolinium-theophylline-7-acetate yield 48%) are obtained. Mp.: 168°–173° C. After recrystallization from a twofold amount of n-propanol the melting point was 195°–198° C.

Analysis: calculated: C% 65.35; H% 5.48; N% 15.24. found: C% 65.01; H% 5.72; N% 15.32.

If in the above method instead of 1-benzal-1,2,3,4-tetrahydro-isoquinoline 1-(3,4-dimethoxy-benzal)-6,7-dimethoxy-1,2,3,4-tetrahydro-isoquinoline is used and the raw product is purified from 96% ethanol, 1-(3,4-dimethoxy-benzal)-6,7-dimethoxy-1,2,3,4-tetrahydro-isoquinolinium-theophylline-7-acetate is obtained with a yield of 42%. Mp.: 195°–196° C.

EXAMPLE 2

3.97 -diethoxy-benzal)-(0.01 mole) of 1-(3,4-didethoxy-benzal)-6,7-diethoxy-1,2,3,4-tetrahydro-isoquinoline and 2.38 g. (0.01 mole) of theophylline-7-acetic acid are dissolved in 32 ml. of ethanol under boiling. The clear solution is crystallized under heating. The precipitated crystals are filtered, covered with a small quantity of ethanol and dried at room-temperature. Thus 6 g. of 1-(3,4-diethoxy-benzal)-6,7-diethoxy-1,2,3,4-tetrahydro-isoquinolinium-theophylline-7-acetate are obtained (94%) yield. Mp.: 160° C. After recrystallization from a tenfold amount of ethanol the melting point is: 160°–161° C.

Analysis:
calculated: C% 62.36; H% 6.48; N% 11.01 found: C% 62.11; H% 6.51; N% 11.27.

Comparative pharmacological tests:

A = 6,7,3',4'-tetra-ethoxy-1-benzal-1,2,3,4-tetrahydroisoquinoline-HCl

B = 6,7,3',4'-tetra-ethoxy-1-benzal-1,2,3,4-tetrahydroisoquinoline-theophylline-7-acetate.

a. Tests on cats

The test was carried out with chloralose (60 mg./kg. urethane/300 mg./kg.) i.p. on narcotized female and male cats of a body weight of 2.5–3.5 kg. A carotis communis of the right side was prepared, in which a cannula was inserted and the cannula was connected with a mercury manometer. A cannula was bound into the trachea and this was connected with a Marey drum, with the aid of which the deflections of respiration were measured. The substances were transferred into the organism through a cannula tied into the v. femoralis. The blood pressure and the respiration were registered on a dark chimographicon.

Blood-pressure

Both compounds A and B decrease blood-pressure. Theophylline is ineffective in the applied doses. Blood-pressure of the animals at the beginning is 120–150 Hgmm.

|   | 1 mg./kg. | 2.0 mg./kg. | 5 mg./kg. |
|---|---|---|---|
| A | −29.4 | −57.3 | −79 |
| B | −21.4 | −51.2 | −68 |

Respiration

Both compounds A and B decrease the deflections of respiration, but compound B to a smaller extent.

|   | 1 mg./kg. | 2 mg./kg. |
|---|---|---|
| A | −20.6 % | −73.5 % |
| B | − 9.5 % | − 6.5 % |

In an infusion of 8 mg./kg./h. none of the compounds caused any considerable alteration.

b. Toxicity on mice

The tests were carried out on starved male mice of a the strain of a the strain CFLP and of body weight of 25–30 g. The compounds were administered intravenously in a volume of 0.1 ml./10 g. and per os in a volume of 0.2 ml./10g. The number of deceased animals within 48 hours was considered. The medial lethal dose was determined on the basis of Behrens-formula

| Results | intravenously | per os |
|---|---|---|
| B | $DL_{50}$: 20.5 mg./kg. | $DL_{50}$: 480 mg./kg. susp. |
| Theophylline-7-acetic acid | $DL_{50}$:>500 mg./kg. | $DL_{50}$:>3000 mg./kg. susp.(0.5 ml./10g.) |
| A | $DL_{50}$: 15 mg./kg. | $DL_{50}$: 350 mg./kg. | c. Toxicity on rats

Tests were carried out on male rats, not previously starved, of the strain CFY and of a body weight of 170–190 g. The compounds were administered intravenously or orally in a dose of 0.3 ml per 100 grams of body weight each 0.1 ml containing 100 mg. of theophylline-7-acetic acid). Compounds A and B were administered in a dose of 0.5 ml./100 g. and theophylline-7-acetic acid in 2 ml./100 g. The medial lethal dose was determined considering the number of deceased animals within 48 hours on the basis of the Behrens-formula.

| Results | intravenously | per os |
|---|---|---|
| B | $LD_{50}$: 19.5 mg./kg. | $DL_{50}$: 540 mg./kg. |
| Theophylline-7-acetic acid | $LD_{50}$:>500 mg./kg. | $DL_{50}$:>5000 mg./kg. susp. |
| A | $LD_{50}$: 14.6 mg./kg. | $DL_{50}$: 540 mg./kg. | d. Investigation of spasmolytic effect on isolated intestine

Tests were carried out according to the method of Magnus on an isolated guinea-pig intestine. An ileum from a guinea-pig of a length of 2.5–3 cm. was hung on a type-bar in a double-vessel on a volume of 30 ml., containing Locke solution at 37° C. Oxygen was circulated through the liquid. The contractions were registered on a dark chimographicon. 100% inhibition concentrations are shown in g./ml.;

|   | A | B | Theophylline-7-acetic acid |
|---|---|---|---|
| carbamylcholine | $3.3 \cdot 10^{-5}$ | $5 \cdot 10^{-5}$ | 0 |
| $6.6 \cdot 10^{-8}$ |  |  |  |
| histamine | $3.3 \cdot 10^{-5}$ | $5 \cdot 10^{-5}$ | 0 |
| $6.6 \cdot 10^{-8}$ |  |  |  | e. Anticonvulsion by electroshock

Tests were carried out on male mice not previously starved, on the strain CFLP and of body weight of 25–30 g. For applying electroshock an instrument of the Nyiro-Zsombok-Kaffka was used. A convulsion including all the four limbs was induced in the mice with a current of 8 mAmp., 0.2 sec. with the aid of corneal electrodes. As a protective effect the elimination of the tonic spasm of the lower limb was considered. The compounds were administered subcutaneously 30 minutes before the electroshock. The median lethal dose was counted according to Litchfield and Wilcoxon. Results:

| Results |   |   |   |
|---|---|---|---|
| B | $ED_{50}$ 36.5 | (32.3 − 41.2) mg./kg. s.c. |
| A | $ED_{50}$ 19 | (14.1 − 25.2) mg./kg. s.c. |

Theophylline-7-acetic acid was ineffective when administered subcutaneously in a dose of 100 mg./kg.

f. Effect on gastric secretory function

Tests were carried out on male rats of a body weight at 140–155 g. previously starved for 48 hours. After opening the abdominal wall in ether narcosis the pylorus of the animals was fixed, then the abdomen was closed. The compounds were administered simultaneously with the operation subcutaneously in a volume of 1.2 ml./100 g. The results were evaluated in the $3^{rd}$ hour after fixing the pylorus. The animals were overnarcotized with ether and the stomach was removed. The quantity of the gastric juice obtained during the test, was measured, given in ml., after centrifugation the pH-value was determined, the free acid was defined by titration with 0.1 n NaOH using methyl-orange, and the total acidity was determined with phenolphthalein. The latter values were given in clinical units.

| Results compound | dose mg./kg. | Medial values of gastric juice | | | | number of animals |
|---|---|---|---|---|---|---|
|  |  | ml. | pH | free acid | total acidity |  |
| control | — | 4.14 | 1.55 | 43.9 | 59.4 | 10 |
| B | 60 | 2.77 | 3.23 | 4.4 | 18.0 | 10 |
| Theophylline-7-acetic acid | 60 | 3.56 | 1.89 | 19.5 | 37.2 | 6 |
| control | — | 4.34 | 1.43 | 61.1 | 73.5 | 10 |
| B | 20 | 3.14 | 1.97 | 16.0 | 29.9 | 10 |
| Theophylline-7-acetic acid | 20 | 3.5 | 1.53 | 35.8 | 51.8 | 7 |
| control | — | 4.48 | 1.76 | 28.7 | 42.9 | 9 |
| A | 20 | 3.28 | 1.98 | 18.8 | 35.5 | 7 |

-continued

| Results compound | dose mg./kg. | Medial values of gastric juice | | | | number of animals |
|---|---|---|---|---|---|---|
| | | ml. | pH | free acid | total acidity | |
| B | 20 | 3.53 | 1.93 | 22.9 | 36.6 | 9 |

What we claim is:
1. 1-benzal-1,2,3,4-tetrahydro-isoquinolinium-theophylline-7-acetate.
2. 1-(3,4-dimethoxy-benzal)-6,7-dimethoxy-1,2,3,4-tetrahydro-isoquinolinium-theophylline-7-acetate.
3. 1-(3,4-diethoxy-benzal)-6,7-diethoxy-1,2,3,4-tetrahydro-isoquinolinium-theophylline-7-acetate.

* * * * *